US009155456B2

(12) United States Patent
Koshikawa

(10) Patent No.: US 9,155,456 B2
(45) Date of Patent: Oct. 13, 2015

(54) IN VIVO EXAMINATION APPARATUS AND CAPSULE ENDOSCOPE

(71) Applicant: OLYMPUS MEDICAL SYSTEMS CORP., Tokyo (JP)

(72) Inventor: Yutaka Koshikawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/927,896

(22) Filed: Jun. 26, 2013

(65) Prior Publication Data

US 2013/0289415 A1   Oct. 31, 2013

Related U.S. Application Data

(63) Continuation of application No. PCT/JP2011/079343, filed on Dec. 19, 2011.

(30) Foreign Application Priority Data

Jan. 17, 2011   (JP) ................................. 2011-007220

(51) Int. Cl.
*A61B 1/04*   (2006.01)
*A61B 1/06*   (2006.01)
*A61B 5/00*   (2006.01)

(52) U.S. Cl.
CPC ............... *A61B 1/041* (2013.01); *A61B 1/0638* (2013.01); *A61B 1/0684* (2013.01); *A61B 5/0059* (2013.01); *A61B 2562/162* (2013.01)

(58) Field of Classification Search
CPC ........................ A61B 1/041; A61B 2562/162
See application file for complete search history.

(56) References Cited

U.S. PATENT DOCUMENTS

2009/0076322 A1*   3/2009   Matsunaga et al. ............ 600/109
2012/0078046 A1*   3/2012   Sasaki et al. .................. 600/109

FOREIGN PATENT DOCUMENTS

| JP | 2006-141711 | 6/2006 |
| JP | 2007-202589 | 8/2007 |
| JP | 2009-066147 | 4/2009 |
| JP | 2009-153621 | 7/2009 |
| JP | 2010-075513 | 4/2010 |

OTHER PUBLICATIONS

International Search Report, dated Jan. 31, 2012, issued in corresponding International Application No. PCT/JP2011/079343.

* cited by examiner

*Primary Examiner* — Unsu Jung
*Assistant Examiner* — Serkan Akar
(74) *Attorney, Agent, or Firm* — Kenyon & Kenyon LLP

(57) ABSTRACT

Provided is an in vivo examination apparatus including an illumination unit emitting two types of illumination light in different wavelength bands; and an image acquisition unit having sensitivity to the wavelength bands of the two types of illumination light. Blood and background tissue have higher reflectances than a predetermined threshold to illumination light in a first wavelength band, blood has a lower reflectance than the threshold to illumination light in a second wavelength band, and a condition $(R1b/R1a)>(R2b/R2a)$ is satisfied, where $R1a$ is the reflectance of the background tissue to the illumination light in the first wavelength band, $R1b$ is the reflectance of the blood to the illumination light in the first wavelength band, $R2a$ is the reflectance of the background tissue to the illumination light in the second wavelength band, and $R2b$ is the reflectance of the blood to the illumination light in the second wavelength band.

2 Claims, 3 Drawing Sheets

IN VIVO EXAMINATION APPARATUS AND CAPSULE ENDOSCOPE

CROSS-REFERENCE TO RELATED APPLICATIONS

This is a continuation of International Application PCT/JP2011/079343, with an international filing date of Dec. 19, 2011, which is hereby incorporated by reference herein in its entirety. This application claims the benefit of Japanese Patent Application No. 2011-007220, the content of which is incorporated herein by reference.

TECHNICAL FIELD

The present invention relates to an in vivo examination apparatus and a capsule endoscope.

BACKGROUND ART

There are known conventional image acquisition apparatuses provided with an illuminating means for radiating light of two wavelengths that have different absorption intensities in blood (for example, see PTLs 1 and 2).

According to such image acquisition apparatuses, an image in which the shapes of blood vessels are extracted by radiating narrow-band light having hemoglobin absorption wavelengths and an image that is acquired when narrow-band light in a wavelength band other than the hemoglobin absorption wavelengths is radiated are separately acquired, thus making it possible to observe a buildup of capillaries etc. in tissue, such as mucosa, without staining.

CITATION LIST

Patent Literature

{PTL 1} Japanese Unexamined Patent Application, Publication No. 2009-66147
{PTL 2} Japanese Unexamined Patent Application, Publication No. 2009-153621

SUMMARY OF INVENTION

Technical Problem

Small-intestine endoscopes and small-intestine capsule endoscopes are often used for patients with unidentified hemorrhages and are used for screening to detect the presence or absence of a hemorrhage at sites in the small-intestine. Thus, it is desired to identify minute hemorrhages with good sensitivity.

An in vivo examination apparatus and a capsule endoscope capable of identifying a minute hemorrhage in the small intestine with good sensitivity to easily detect the presence or absence of a hemorrhage in patients with unidentified hemorrhages are provided.

Solution to Problem

According to a first aspect, the present invention provides an in vivo examination apparatus including: an illumination unit that emits illumination light in a first wavelength band having a center wavelength of about 600 nm and illumination light in a second wavelength band having a center wavelength of about 415 nm; an image acquisition unit that is formed of an imaging optical system and an imaging element that has sensitivity to light in the two wavelength bands; a storage unit that stores images acquired by the image acquisition unit; and a control unit that controls the illumination unit to make the illumination unit emit illumination light in the two wavelength bands alternately in a time-division manner and that controls the image acquisition unit to make the image acquisition unit output, to the storage unit, images acquired when the illumination light in the two wavelength bands is radiated, in which a bandwidth of the first wavelength band is wider than a width in which effective sensitivity widths, which are wavelength ranges in which the sensitivity is 25% or more of a sensitivity peak in each region, overlap at a shorter wavelength side of a R region and a longer wavelength side of a G region; and a white-light image is generated from the illumination light in the first wavelength band and the illumination light in the second wavelength band by acquiring, with pixels of the imaging element having sensitivity to the R region, independent luminance information in the R region at a longer wavelength side of the first wavelength band, acquiring, with pixels of the imaging element having sensitivity to the G region, independent luminance information in the G region at a shorter wavelength side of the first wavelength band, and acquiring independent luminance information in the respective R, G, and B regions; and blood and background tissue have higher reflectances than a predetermined threshold with respect to illumination light in the first wavelength band emitted from the illumination unit, blood has a lower reflectance than the threshold with respect to illumination light in the second wavelength band, and a following condition is satisfied, $$(R1b/R1a) > (R2b/R2a),$$

where R1a is the reflectance of the background tissue with respect to the illumination light in the first wavelength band, R1b is the reflectance of the blood with respect to the illumination light in the first wavelength band, R2a is the reflectance of the background tissue with respect to the illumination light in the second wavelength band, and R2b is the reflectance of the blood with respect to the illumination light in the second wavelength band.

Furthermore, according to a second aspect, the present invention provides a capsule endoscope including: a capsule-like chassis; and the above-described in vivo examination apparatus that is disposed in the chassis in a hermetically sealed manner.

DESCRIPTION OF EMBODIMENTS

An in vivo examination apparatus 1 according to an embodiment of the present invention will be described below with reference to the drawings.

Figure 1:
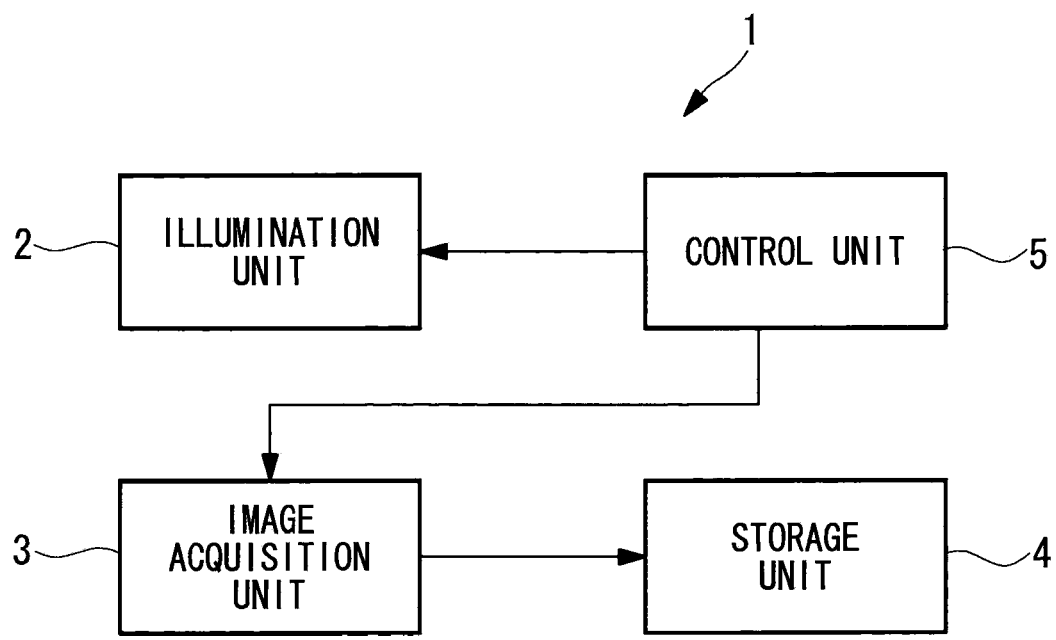
FIG. 1 is a block diagram showing an in vivo examination apparatus according to an embodiment of the present invention.

As shown in FIG. 1, the in vivo examination apparatus 1 of this embodiment includes an illuminating unit 2 that emits illumination light onto a living body, an image acquisition unit 3 that acquires reflected light from the living body, a storage unit 4 that stores images acquired by the image acquisition unit 3, and a control unit 5 that controls these units. The image acquisition unit 3 is provided with an imaging optical system and an imaging element.

Figure 2:
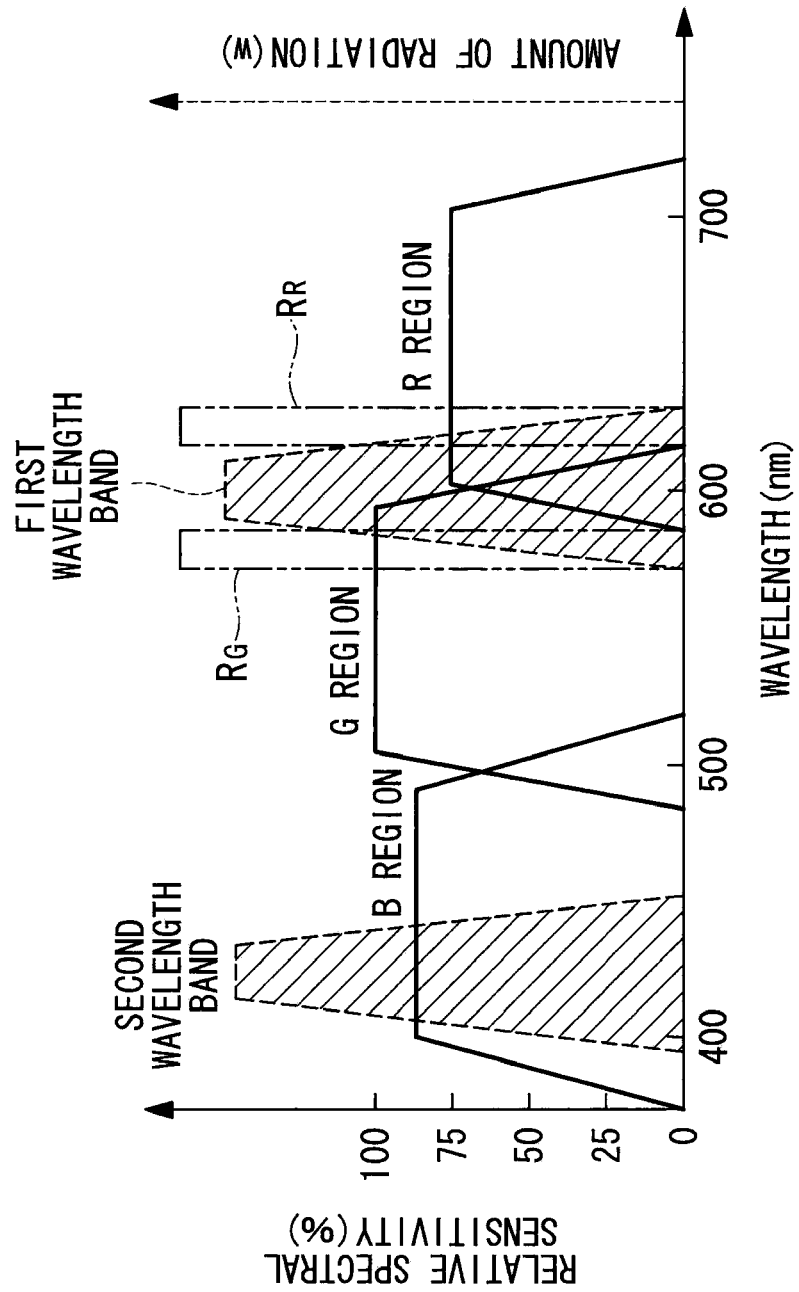
FIG. 2 is a graph showing the wavelength characteristics of an illumination unit and an image acquisition unit of the in vivo examination apparatus shown in FIG. 1.

The illuminating unit 2 emits illumination light in two different wavelength bands. As shown in FIG. 2, a first wavelength band has a center wavelength of about 600 nm and has a bandwidth of about 40 nm, for example. A second wavelength band has a center wavelength of about 415 nm and has a bandwidth of about 40 nm, for example. Here, the bandwidth is the wavelength range in which the intensity is 25% or more of the intensity at the peak wavelength.

The spectral sensitivity of the image acquisition unit 3 is the total of the spectral sensitivity of the imaging element and the spectral transmission characteristics of the imaging optical system (including a color compensating filter if any), and, in this embodiment, as shown in FIG. 2, the image acquisition unit 3 has sensitivities for a B region from about 380 to 520 nm, a G region from about 460 to 610 nm, and a R region from about 590 to 740 nm. The sensitivity width is the wavelength range in which the sensitivity is 25% or more of the sensitivity peak (in this embodiment, the sensitivity at about 550 nm). Furthermore, in FIG. 2, reference symbol $R_R$ denotes a wavelength band that provides independent luminance information in the R region, in the first wavelength band, and reference symbol $R_G$ denotes a wavelength band that provides independent luminance information in the G region.

Figure 3:
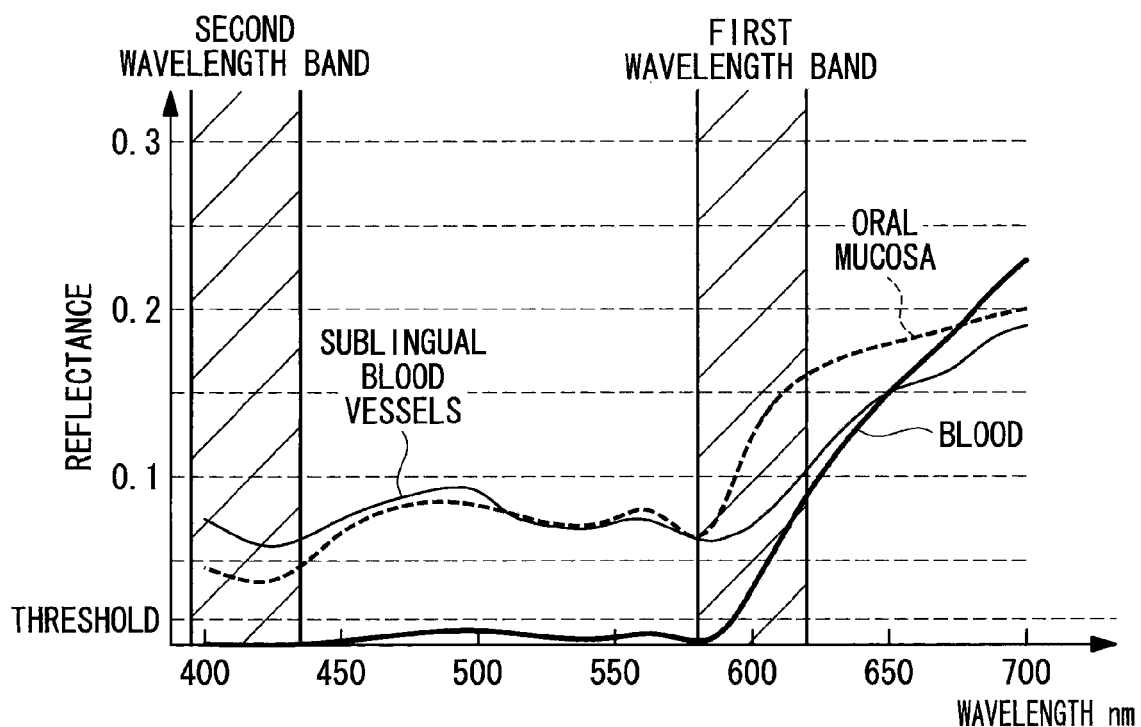
FIG. 3 is a graph showing example reflectance characteristics of a living body.

FIG. 3 shows the reflectance characteristics of pig's blood, sublingual blood vessels, and oral mucosa. In the reflectance characteristics, oral mucosa (background tissue), sublingual blood vessels (background tissue), and blood have reflectances higher than a predetermined threshold, with respect to illumination light in the above-described first wavelength band. Furthermore, blood has a reflectance lower than the threshold, with respect to illumination light in the second wavelength band.

When it is assumed that the reflectance of the background tissue with respect to illumination light in the first wavelength band is R1a, the reflectance of the blood with respect to illumination light in the first wavelength band is R1b, the reflectance of the background tissue with respect to illumination light in the second wavelength band is R2a, and the reflectance of the blood with respect to illumination light in the second wavelength band is R2b, the following conditional equation is satisfied, $$(R1b/R1a) > (R2b/R2a).$$

The control unit 5 controls the illuminating unit 2 to make it alternately emit illumination light in the first wavelength band and illumination light in the second wavelength band in a time-division manner.

Furthermore, the control unit 5 controls the image acquisition unit 3 to make it output, to the storage unit 4, images acquired when the illumination light in the first wavelength band and the illumination light in the second wavelength band are emitted.

The operation of the thus-configured in vivo examination apparatus 1 of this embodiment will be described below.

According to the in vivo examination apparatus 1 of this embodiment, when the control unit 5 actuates the illuminating unit 2 to alternately radiate illumination light in the first wavelength band and illumination light in the second wavelength band onto the living body, reflected light that returns after being reflected at the living body is acquired by the image acquisition unit 3, thus acquiring reflected-light images.

With respect to illumination light in the second wavelength band, the reflectance of the background tissue is higher than the threshold, and the reflectance of the blood is lower than the threshold. Thus, there is a possibility that a hemorrhage appears as a dark area in the image that is acquired when the illumination light in the second wavelength band is radiated. On the other hand, a portion of the living body that is located away from the illuminating unit 2 also appears as a dark area in the image. Therefore, by using only the image that is acquired when illumination light in the second wavelength band is radiated, it is difficult to determine whether a dark area appears in the image because of a hemorrhage or a large distance from the illuminating unit 2.

On the other hand, with respect to illumination light in the first wavelength band, the blood and the background tissue both have reflectances higher than the threshold. Thus, a hemorrhaging area that is located near the illuminating unit 2 does not appear as a dark area in the image, thus acquiring an image that is somewhat bright.

Specifically, if an area that is dark in the image acquired when illumination light in the second wavelength band is radiated is bright in the image acquired when illumination light in the first wavelength band is radiated, it is possible to determine that the area is suspected to have a hemorrhage.

Furthermore, if an identical area is dark in both the image acquired when illumination light in the first wavelength band is radiated and the image acquired when illumination light in the second wavelength band is radiated, it is possible to determine that the illumination light does not reach that area because of a large distance between the illuminating unit 2 and the living body.

According to the in vivo examination apparatus 1 of this embodiment, it is possible to easily pick out an image indicating a suspected hemorrhage from the acquired images and to significantly reduce the time required to analyze a huge number of images after image acquisition (the time required for interpreting radiograms). In contrast, if an image indicating a suspected hemorrhage is picked out in real time based on the acquired images, it is possible to reduce the number of images to be stored.

Furthermore, in this embodiment, because a wavelength band that is included in both the G region and the R region of the imaging element, which is formed of a color CCD, is selected as the first wavelength band, it is possible to perform spectral estimation processing from the two acquired images to acquire three types of images of the R region, the G region, and the B region, and to generate a white-light image through image estimation processing.

Furthermore, in this embodiment, the following features are provided in order to acquire a good white-light image. The bandwidth of the first wavelength band is wider than the width in which the effective sensitivity widths (wavelength ranges in which the sensitivity is 25% or more of the sensitivity peak in each region) overlap at a shorter wavelength side of the R region and a longer wavelength side of the G region. With this configuration, it is possible to acquire substantially independent luminance information in the G region at the shorter wavelength side of the first wavelength band and substantially independent luminance information in the R region at the longer wavelength side of the first wavelength band. Thus, it is possible to acquire independent luminance information in the R, G, and B regions and to acquire a good white-light image by performing color reproduction processing, such as spectral estimation.

Furthermore, as shown in FIG. 3, because the living body has higher reflectance in the red region, when the illumination given to the G region is weighted, luminance information can be acquired in the R region and the G region at an intensity ratio having better balance. Specifically, when the wavelength at the shorter wavelength side of the first wavelength band (wavelength at which the intensity is 25% of the intensity at the peak wavelength) is set at a shorter wavelength side of the effective sensitivity wavelength limit at the shorter wavelength side of the R region (wavelength at which the sensitivity is 25% of the sensitivity peak), an even better white-light image can be acquired.

In particular, when the small intestine is selected as the living tissue to be observed, the observed scene is stable because a change in biological structure is small compared with that of the stomach or large intestine, thus making it possible to sufficiently estimate a white-light image with illumination light in two narrow wavelength bands.

Note that, in the in vivo examination apparatus 1 of this embodiment, although images to be used to confirm the presence of a hemorrhaging area are stored in the storage unit 4, instead of this, it is possible to adopt a configuration in which a determination unit (not shown) that determines the presence or absence of a hemorrhaging area from acquired images is provided, and only images from which the determination unit determines that there is a suspected hemorrhaging area are stored in the storage unit 4.

Figure 4:
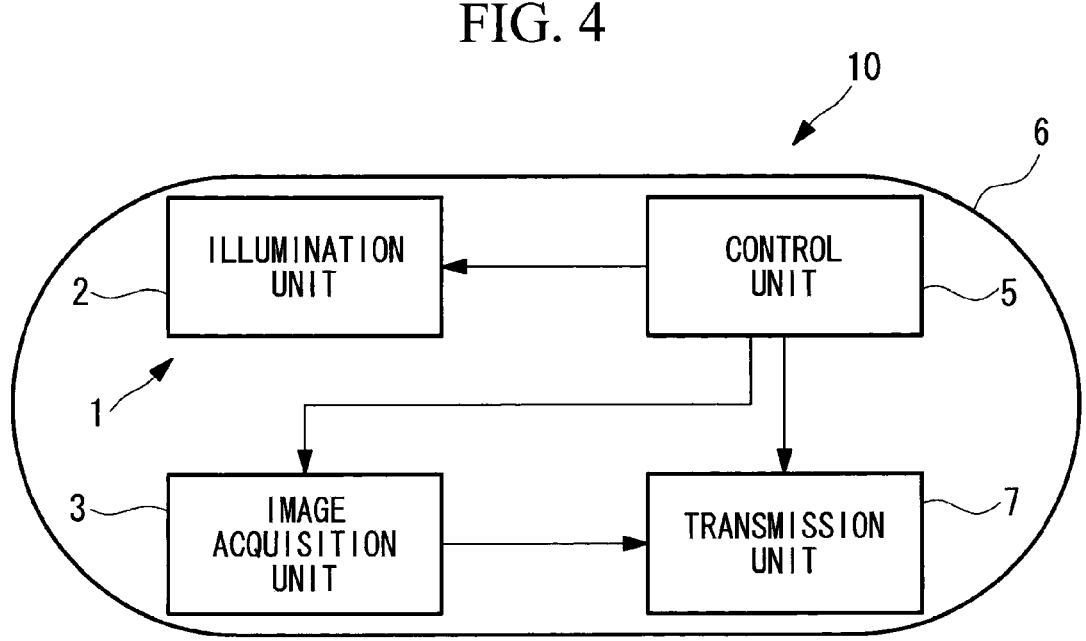
FIG. 4 is a block diagram showing a capsule endoscope in which the in vivo examination apparatus shown in FIG. 1 is accommodated in a chassis.

Furthermore, as shown in FIG. 4, it is possible to construct a capsule endoscope 10 in which the in vivo examination apparatus 1 of this embodiment is accommodated in a clear capsule-like chassis 6. FIG. 4 shows a configuration in which a transmission unit 7 that transmits acquired images toward the outside of the body is provided instead of the storage unit 4.

In the case of the capsule endoscope 10, because it is driven by a battery (not shown), an advantageous effect is afforded in that two types of monochromatic LEDs can be used as the illuminating unit 2, which radiates illumination light in two narrow wavelength bands, as in the in vivo examination apparatus 1 of this embodiment, thus reducing the battery consumption. That is to say, by using only illumination from the two types of monochromatic LEDs, white-light images can be acquired through image estimation. Compared with a case in which a white LED with low luminance efficiency is used, the battery consumption can be reduced.

Furthermore, if the battery capacity is sufficient, the capacity can be reduced, and, in that case, there is an advantage in that a reduction in size of the chassis 6 and a reduction in size and weight of the whole apparatus can be achieved.

Furthermore, when the result of determination as to whether a hemorrhaging area exists is fed back, and image acquisition is performed again for the suspected hemorrhaging area, it is also possible to increase the intensity of illumination light by using power corresponding to the reduction in battery consumption.

According to the first aspect of the present invention, when the two types of illumination light emitted from the illumination unit are radiated onto the body tissue, the illumination light in the first wavelength band is reflected at blood and background tissue and is acquired by the imaging element, which has sensitivity to the first wavelength band. On the other hand, the illumination light in the second wavelength band is absorbed more in blood, and its reflected light is acquired by the imaging element, which has sensitivity to the second wavelength band. Because the wavelength bands of the two types of illumination light are selected so as to satisfy the above-described condition, if an image of the reflected light in the second wavelength band is dark, from the brightness of the image of the reflected light in the first wavelength band, it is possible to easily determine whether it is dark because of a large distance from the illumination unit to the body tissue or because of a hemorrhage, thus clearly identifying a minute hemorrhage to easily detect the hemorrhage.

In the above-described first aspect, the image acquisition unit may be provided with an imaging optical system and an imaging element; the imaging element may be provided with pixels having sensitivity to a R region, a G region, and a B region; the first wavelength band may be included in both the G region and the R region of the imaging element; and the second wavelength band may be included in the B region of the imaging element.

By doing so, it is possible to adopt, as the illumination unit, two types of monochromatic LEDs, i.e., a monochromatic LED with wavelengths included in both the G region and the R region of the imaging element and a monochromatic LED with wavelengths included in the B region of the imaging element. By adopting the monochromatic LEDs with good luminance efficiency, it is possible to reduce the power consumption compared with general white LEDs, thus extending the battery life and reducing the size.

Furthermore, when the small intestine is selected as the body tissue to be observed, the observed scene is stable because a change in biological structure is small compared with that of the stomach or large intestine, thus making it easy to perform spectral estimation processing even with illumination light from the two types of monochromatic LEDs. Then, it is possible to acquire three types of images of the R region, the G region, and the B region from the illumination light emitted from the two types of monochromatic LEDs and to perform estimation processing for a white-light image.

Furthermore, according to a second aspect, the present invention provides a capsule endoscope including: a capsule-like chassis; and the above-described in vivo examination apparatus that is disposed in the chassis in a hermetically sealed manner.

According to the second aspect of the present invention, in the capsule endoscope, which has the above-described in vivo examination apparatus provided in the capsule-type chassis in a hermetically sealed manner, by using the two types of monochromatic LEDs, it is possible to acquire a white-light image while reducing the energy consumption, compared with a case in which a white LED with poor luminance efficiency is used. That is to say, it is possible to reduce the battery consumption, which extends the image-acquisition time of the capsule endoscope, to which power is not supplied from the outside, or to achieve a reduction in size of the chassis due to a reduction in battery size.

According to the present invention, an advantageous effect is afforded in that a minute hemorrhage in the small intestine is identified with good sensitivity to easily detect the presence or absence of a hemorrhage in patients with unidentified hemorrhages.

REFERENCE SIGNS LIST 1 in vivo examination apparatus
2 illumination unit
3 image acquisition unit
6 chassis
10 capsule endoscope

The invention claimed is:
1. An in vivo examination apparatus comprising:
an illumination device that emits illumination light in a first wavelength band having a center wavelength of 600 nm and illumination light in a second wavelength band having a center wavelength of 415 nm;

an image acquisition unit that is formed of an imaging optical system and an imaging element that has sensitivity to light in the two wavelength bands;

a storage unit that stores images acquired by the image acquisition unit; and a control unit that controls the illumination device to make the illumination device emit illumination light in the two wavelength bands alternately in a time-division manner and that controls the image acquisition unit to make the image acquisition unit output, to the storage unit, images acquired when the illumination light in the two wavelength bands is radiated, wherein a bandwidth of the first wavelength band includes wavelength ranges, in which the sensitivity is 25% or more of a sensitivity peak, in each of a R region and a G region overlap at a shorter wavelength side of the R region and a longer wavelength side of the G region;

a white-light image is generated from the illumination light in the first wavelength band and the illumination light in the second wavelength band by acquiring, with pixels of the imaging element having sensitivity to the R region, independent luminance information in the R region at a longer wavelength side of the first wavelength band, acquiring, with pixels of the imaging element having sensitivity to the G region, independent luminance information in the G region at a shorter wavelength side of the first wavelength band, and acquiring independent luminance information in the respective R, G, and B regions; and blood and background tissue have higher reflectances than a predetermined threshold with respect to illumination light in the first wavelength band emitted from the illumination device, the blood has a lower reflectance than the threshold with respect to illumination light in the second wavelength band, and a following condition is satisfied, $$(R1b/R1a) > (R2b/R2a),$$

where R1a is the reflectance of the background tissue with respect to the illumination light in the first wavelength band, R1b is the reflectance of the blood with respect to the illumination light in the first wavelength band, R2a is the reflectance of the background tissue with respect to the illumination light in the second wavelength band, and R2b is the reflectance of the blood with respect to the illumination light in the second wavelength band.

2. A capsule endoscope comprising:

a capsule-like chassis; and an in vivo examination apparatus according to claim 1 that is disposed in the chassis in a hermetically sealed manner.

* * * * *